United States Patent [19]

Sank et al.

[11] Patent Number: 4,912,111

[45] Date of Patent: Mar. 27, 1990

[54] USE OF MINOXIDIL FOR WOUND HEALING

[75] Inventors: Anthony C. Sank; George R. Martin, Mich.; NIDR, NIH, Bethesda, Md. Steven R. Ledbetter, Kalamazoo, Mich.

[73] Assignees: The Upjohn Company, Kalamazoo, Mich.; Nidr, Nih, Bethesda, Md.

[21] Appl. No.: 281,129

[22] Filed: Dec. 7, 1988

[51] Int. Cl.$^4$ .......................................... A61K 31/505
[52] U.S. Cl. ..................................................... 514/256
[58] Field of Search ........................................ 514/256

[56] References Cited

U.S. PATENT DOCUMENTS 4,139,619  2/1979  Chidsey ................................. 424/45
4,596,812  6/1986  Chidsey et al. ..................... 514/256

OTHER PUBLICATIONS

Murad et al., "Supression of Fibroblast Proliferation and Lysyl Hydroxylase Activity by Minoxidil", J. Biol Chem., vol. 262, No. 25., pp. 11973–11978 (1987).

Schultz, et al., "Epithelial Wound Healing Enhances by Transforming Growth Factor-α and Vaccinia Growth Factor", Science, vol. 235, pp. 350–352 (1987).

Murad, S., et al., "Selective Depression of Lysyl Hydroxylase Activity in Human Skin Fibroblasts by Minoxidil", J. Invest. Derm., vol. 86, No. 4, p. 496 (Apr. 1986).

Murad, S., et al., "suppression of Fibroblast Proliferation and Lysyl Hydroxylase Activity by Minoxidil", J. Biol. Chem., vol. 262, No. 25, pp. 11973–11978 (1987).

Pinnell, et al., "Effects of Minoxidil on Cultured Human Skin Fibroblasts", Dermatologica, vol. 175, Suppl. 2, pp. 12–18 (1987).

*Primary Examiner*—Douglas W. Robinson
*Assistant Examiner*—Zehyeh A. Fay
*Attorney, Agent, or Firm*—Donald L. Corneglio

[57] ABSTRACT

A method for the promotion or acceleration of wound healing by a treatment with minoxidil is disclosed. The minoxidial can be administered by topical application, oral administration, injection or any combination thereof. Treatment with minoxidil is effective for promoting the migration of epithelial cells in a wound or in tissues such as cornea and the like. Methods for identifying binding sites for minoxidil in cells based on their affinity for the compound in attachment or chemotactic assays are described.

14 Claims, 6 Drawing Sheets

FIG. 3

VARIATION IN THE
MIGRATORY RESPONSE TO MINOXIDIL DEPENDING ON ITS
PRESENCE IN THE BOTTOM OR TOP OR BOTH CHAMBERS

| ADDITION | CHEMOTAXIS ($um^2 \times 10^{-3}$) |
|---|---|
| BSA (CONTROL) | 7.1 |
| EGF 100 (ng/ml) | 32.4 |
| BOTTOM-MINOXIDIL 1(ug/ml) | 24.8 |
| MINOXIDIL 10 | 30.2 |
| MINOXIDIL 100 | 30.1 |
| TOP AND BOTTOM -MINOXIDIL 100 | 6.1 |
| TOP- MINOXIDIL 100 | 15.4 |

FIG. 4

RELATION OF CYCLIC AMP, A CALCIUM CHANNEL BLOCKER AND A CALCIUM AGONIST IN THE CELLULAR RESPONSE TO MINOXIDIL

| ADDITION | CHEMOTAXIS ($um^2 \times 10^{-3}$) |
|---|---|
| BSA (CONTROL) | 7.1 |
| EGF 100 | 32.4 |
| MINOXIDIL 100 | 30.1 |
| EGF 100 + cAMP/IBMX | 35.7 |
| MINOXIDIL 100 + cAMP/IBMX | 39.9 |
| MINOXIDIL 100 + VERAPAMIL | 24.5 |
| MINOXIDIL 100 + BAY K8644 ($Ca^{++}$ Agonist) | 18.8 |

USE OF MINOXIDIL FOR WOUND HEALING

BACKGROUND OF THE INVENTION

The present invention is directed toward the use of minoxidil to support and to modulate the healing of wounds. Generally, the present invention is useful for the improvement or acceleration of the healing of wounds.

Minoxidil is a synthetic chemical with proven efficacy as a hypotensive agent and as a stimulant of hair growth. Thus it acts on different kinds of cells and induces different phenomena. These have useful sequelae in the treatment of hypertension and for enhancing hair growth.

The healing of wounds is a complex process. Certain reactions are initiated almost immediately after wounding including the clotting of blood and the aggregation of platelets. These steps are important as they stop the bleeding and they also initiate the first steps in the repair process. Cellular migrations are observed within the first day or two with the arrival of phagocytic cells such as neutrophils and macrophages. A day or two later, fibroblastic cells enter the wound and begin to produce the connective tissue components, including collagen, necessary for restoration of the dermal tissue. Endothelial cells also enter the wound and form the capillaries that restore the blood supply to the area.

Following the formation of the clot, epidermal cells at the margin of the wounds, as well as epithelial cells and organelles such as hair follicles, begin to migrate out from the edge of the wound and from the remnants of hair follicles in the wounded area. With minor wounds and in most other wound heating situations, these migrations of epithelial cells continue until the wounded area is completely covered by the epidermal cells. These cells are also known as keratinocytes.

Several studies have shown that the addition of exogenous factors to the wound accelerate wound healing. These wound stimulatory factors are polypeptides and can increase the formation of fibrous tissue. Also one such growth factor TGFα, Schultz, et al., "Epithelial Wound Healing Enhances by Transforming Growth Factoralpha and Vaccinia Growth Factor", Science 235:350-2 (1987), has been reported to increase the epithelialization of experimental wounds. Clinically, wound healing is impaired or abnormal in a variety of conditions including diabetes, aging, following burns and in decubital conditions. The importance of the proper completion of each step in the wound healing process is illustrated in burns where epidermal coverage of the burn when delayed is associated with infection, fluid loss and abnormal scaring.

The sources of cells involved in the healing of skin include fibroblasts, smooth muscle cells and endothelial cells in the dermis and associated structures. Keratinocytes from the borders of the wound as well as epithelial cells from hair follicles are the major sources of the cells which restore the epidermis. In a small cut, the scar may be formed from fibroblasts, endothelial cells and epidermal cells which migrate in from the normal tissue around the wound. In a burn, smooth muscle cells may contribute the major portion of the dermis, while epithelial cells from hair follicles may provide much of the epidermal coverage over the tissue.

INFORMATION DISCLOSURE

Minoxidil is reported to selectively depress lysyl hydroxylase activity in cultured human skin fibroblast, Murad, S., et al., "Selective Depression of Lysyl Hydroxylase Activity in Human Skin Fibroblasts", J. Invest. Derm., Vol. 36, pages 4963 (1986). This finding, by Pinnell and colleagues, suggests that minoxidil could be used as an antifibrotic agent, Murad, S., et al., "Suppression of Fibroblast Proliferation and Lysyl Hydroxylase Activity by Minoxidil", J. Biol. chem., Vol. 262, pages 11973–78, (1987) and Pinnell, et al., "Effects of Minoxidil on Cultured Human Fibroblasts", Dermatologica, Vol. 175, Suppl. 2, pages 12–18 (1987) and therefore have therapeutic benefit in conditions characterized by an overproliferation of connective tissue. Because lysyl hydroxylase activity has never been shown to influence or in any way contribute to cellular chemotaxis, the publications by Pinnell and colleagues do not disclose or suggest to a person skilled in the art that minoxidil would stimulate directed migration of skin keratinocytes or fibroblasts, or that minoxidil would accelerate the closure of wounds.

Topical compositions of minoxidil are known for treatment of baldness and are disclosed in U.S. Pat. Nos. 4,139,619 and 4,596,812. Also, various salts and derivatives of minoxidil, as well as associated methods, are known and disclosed in U.S. Pat. Nos. 3,382,247, 3,461,461, 3,644,364 and 4,287,338 and published by J. M. McCall, et al., Journal of Organic Chemistry, Vol. 40, page 3304 (1975).

SUMMARY OF THE INVENTION

In one aspect, the invention is a method for improving or accelerating the healing of wounds comprising treatment with minoxidil. The treatment can be a topical composition of minoxidil applied directly to the wound, preferably the topical composition comprises from about 0.01% to about 1% minoxidil. The treatment can also comprise an injection of minoxidil in an effective amount to accelerate the healing of the wound or an oral administration of minoxidil. Generally, an oral administration comprises from about 5 to about a 100 mg dose per day of minoxidil.

Furthermore, the treatment can be a combination of topical, injection or oral administration of minoxidil.

In yet another aspect, the present invention is a method for promoting the migration of epithelial cell comprising the treatment of such epithelial cells with minoxidil. The method can comprise a topical composition of minoxidil applied directly to the epithelial cells or the vicinity of the epithelial cells to be effected. Generally, the topical composition comprises from about 0.01% to about 1% minoxidil. The method can also comprise an injection of minoxidil in an effective amount to promote the migration of the epithelial cells or an oral administration of minoxidil. Generally, an oral administration comprises from about 5 to about a 100 mg dose per day of minoxidil. Furthermore, the treatment can comprise any combination of topical, injection or oral administration of minoxidil.

The present invention has found minoxidil to be chemotactic for keratinocytes and for fibroblasts, additionally minoxidil is able to stimulate the general mobility of these cells. It has also been demonstrated that these cells will adhere to minoxidil demonstrating that the cells have minoxidil receptors or binding groups on their surfaces.

BRIEF DESCRIPTION OF THE DRAWINGS

FIG. 3 shows the response of human keratinocytes (epidermal cells) in chemotaxis assays in Boyden chambers. Minoxidil was placed in some experiments in the bottom compartment, in others in the top and in others in both top and bottom compartments.

FIG. 4 shows studies which relate to the mechanism of action of minoxidil in promoting chemotaxis. In addition to minoxidil, EGF and BSA, cyclic AMP plus IBMX were added to some samples, while verapamil (a calcium channel blocker), BAY K8644 (a calcium agonist) were added to the samples in other studies.

DETAILED DESCRIPTION OF THE INVENTION

Figure 1:
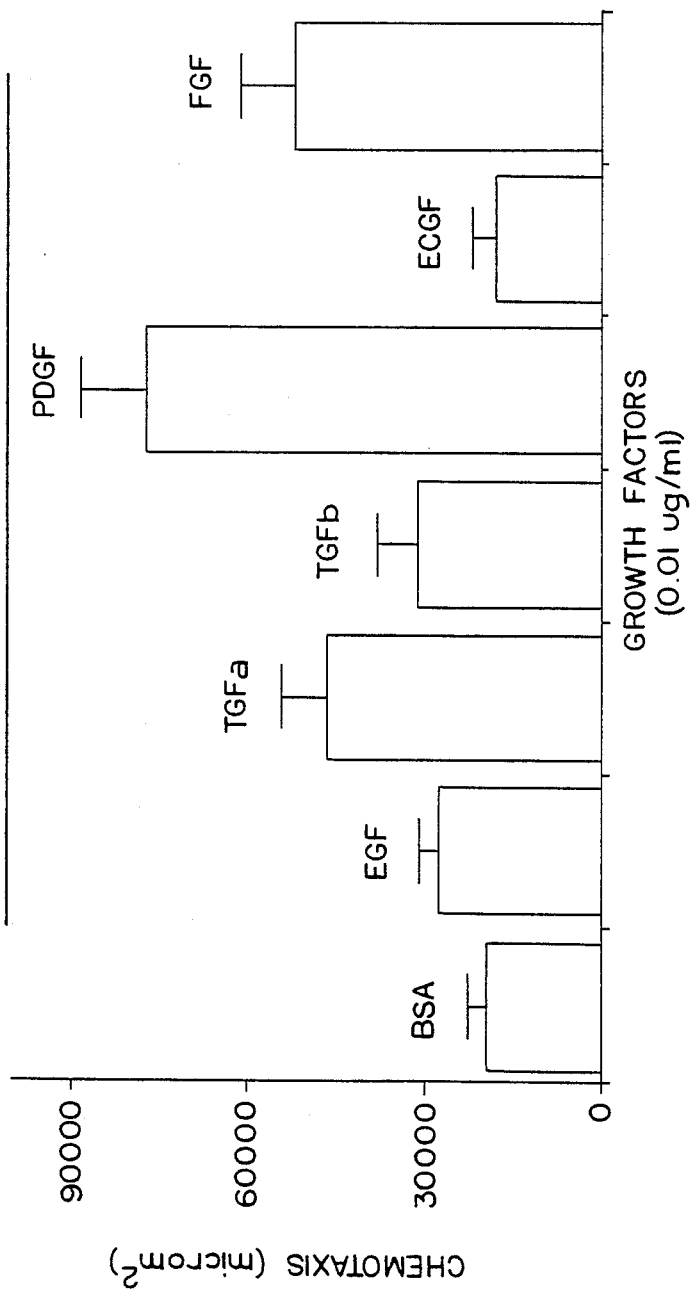
FIG. 1 shows the migration of human keratinocyte (epidermal) cells in chemotaxis assays as they respond to BSA (bovine serum albumin), EGF (epidermal growth factor 10 ng/ml), TGFα (transforming growth factor alpha 10 ng/ml), TGFβ (transforming growth factor beta 10 ng/ml), PDFG (platelet derived growth factor 10 ng/ml), ECGF (endothelial cell growth factor 10 ng/ml), FGF (fibroblast growth factor 10 ng/ml).

The present invention is directed toward the use of minoxidil to induce the migration of epidermal and other cells and thus to improve the healing and restoration of skin and other tissues damaged by trauma, burns, aging, environmental factors etc. The epidermal cells referred to here include keratinocytes and epithelial cells in hair follicles which serve as a source of cells for the coverage of lesions of skin and other organs such as the cornea.

The active component of the subject compositions is minoxidil which chemically is 6-amino-1,2-dihydrohydroxy-2-imino-4-piperidinopyrimidine and analogs thereof. The preparation of these compounds are described in U.S. Pat. Nos. 3,382,247, 3,461,461 and 3,644,364 and J. M. McCall, et al., Journal of Organic Chemistry, Vol. 40, page 3304 (1975) all of which are hereby incorporated by reference. Related compounds are sulfoxypyrimidinium, -pyridinium, and -triazinium which are described in U.S. Pat. No. 4,287,338 herein incorporated by reference. Hereinafter, the term "minoxidil" means any of the various forms of 6-amino-1,2-dihydro-hydroxy-2-imino-4-piperidinopyrimidine, derivatives and analogs thereof.

In one preferred composition, the various minoxidil compounds were synthesized by The Upjohn Company, Kalamazoo, Mich., and were dissolved in acetone plus physiological saline 0.15M NaCl, plus 0.05M phosphate buffer, pH 7.4. Samples dissolved in acetone were diluted with media to a maximum of 1% acetone.

Human keratinocytes were grown in an incubator maintained at 37° C. in 95% air - 5% $CO_2$. Keratinocytes cultures at near confluence were rinsed with phosphate buffered saline PBS and removed from the dish with trypsin (0.025%) in PBS.

To measure cell migration, chemotaxis assays were carried out. Polycarbonate filters (12 micron pore size) were coated with type IV collagen (10 micrograms/filters) and placed in a modified Boyden chamber. Cells (human keratinocytes) were harvested and prepared as described above, and $3.0 \times 10^5$ cells in 0.8 ml were placed in the upper compartment of the Boyden chamber. The lower compartment of the Boyden chamber contained the chemoattractants including various growth factors, minoxidil or related compounds dissolved in serumfree Eagles #2 Medium with 0.1% BSA (0.2 ml). The chambers were then incubated for six hours at 37° C., 5% $CO_2$ and 95% air. The cells which had attached to the upper side of the filter were mechanically removed. The cells which had migrated to the lower side of the filter were fixed in methanol, and then strained with hematoxylin and eosin. Each sample was assayed in quadruplicate, and the cells in at least 10 microscopic fields per filter were counted.

Figure 2:
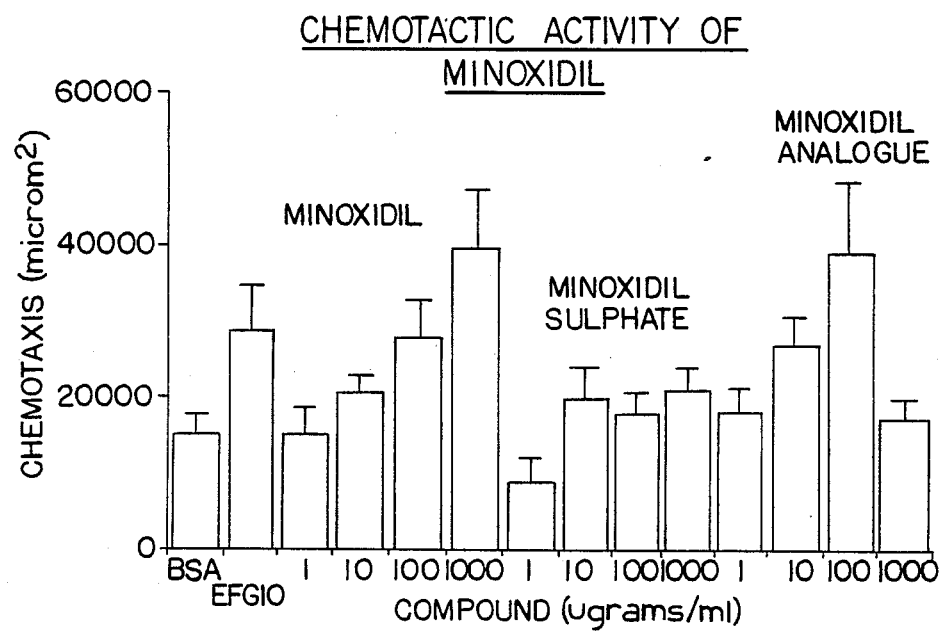
FIG. 2 shows the chemotactic response of human keratinocytes (epidermal cells) to minoxidil, minoxidil sulfate and a minoxidil analogue. BSA indicates the migration of the cells in response to this protein which was added to all samples. EGF at 100 ng/ml was added as a known positive chemoattractant.

As shown in FIG. 1, human keratinocytes are able to undergo directed movement in response to certain growth factors, particularly TGF alpha, PDGF and FGF. Other growth factors EGF, ECGF and TGF beta show lesser activity to mobilize the cells. At higher levels of EGF, i.e., 100 ng/ml, comparable positive activity was observed (FIG. 2). When minoxidil was tested for chemotactic activity, it caused a dose dependent migration of the keratinocytes over the range of 10–1000 μg/ml. An analogue of minoxidil, 6-amino-1,2-dihyro-1-hydroxy-2-imino-pyrimidine, showed activity at 10 and 100 μg/ml.

The migration of the keratinocytes in response to minoxidil was assessed to determine chemoattractant activity (FIG. 3). To make this assessment, the response of the cells to minoxidil when it was incorporated into the top, the bottom or both chambers was tested. In all cases, the keratinocytes were placed in the top chamber. Minoxidil when placed in the lower chamber induced the expected migration of the cells as shown in FIG. 2. When minoxidil was placed in equal amounts in both chambers, little or no increase in migration was observed indicating that in the absence of a gradient migration was not occurring.

Some response was induced by minoxidil when it was placed with the cells in the top compartment. Such responses are typical of chemotactic factors which are able to stimulate random motion in cells. These results are consistent with minoxidil being both chemotactic and a stimulator of random cellular migrations.

Figure 5:
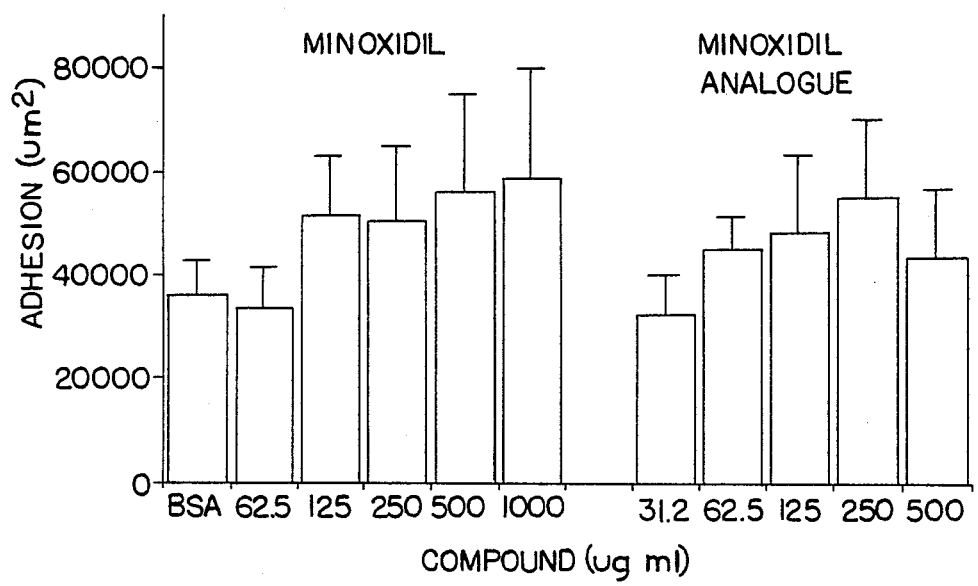
FIG. 5 shows that human keratinocytes have the ability to bind to minoxidil and to a lesser extent to an analogue of minoxidil. In these studies, the compounds were dried onto a plastic petri dish and the ability of these substrates to allow cells to bind to immobilized minoxidil was tested.

As shown in FIG. 5, the attachment of keratinocytes is increased by coating the plastic dish with various concentrations of minoxidil. The minoxidil analogue had a similar but somewhat lesser activity. The fact the the keratinocytes bind to minoxidil indicates that they have binding groups on their surface for minoxidil. Since chemotaxis is often mediated via cell surface receptors which bind the attractant, attachment and chemotaxis could be mediated by the same cellular receptors.

Figure 6:
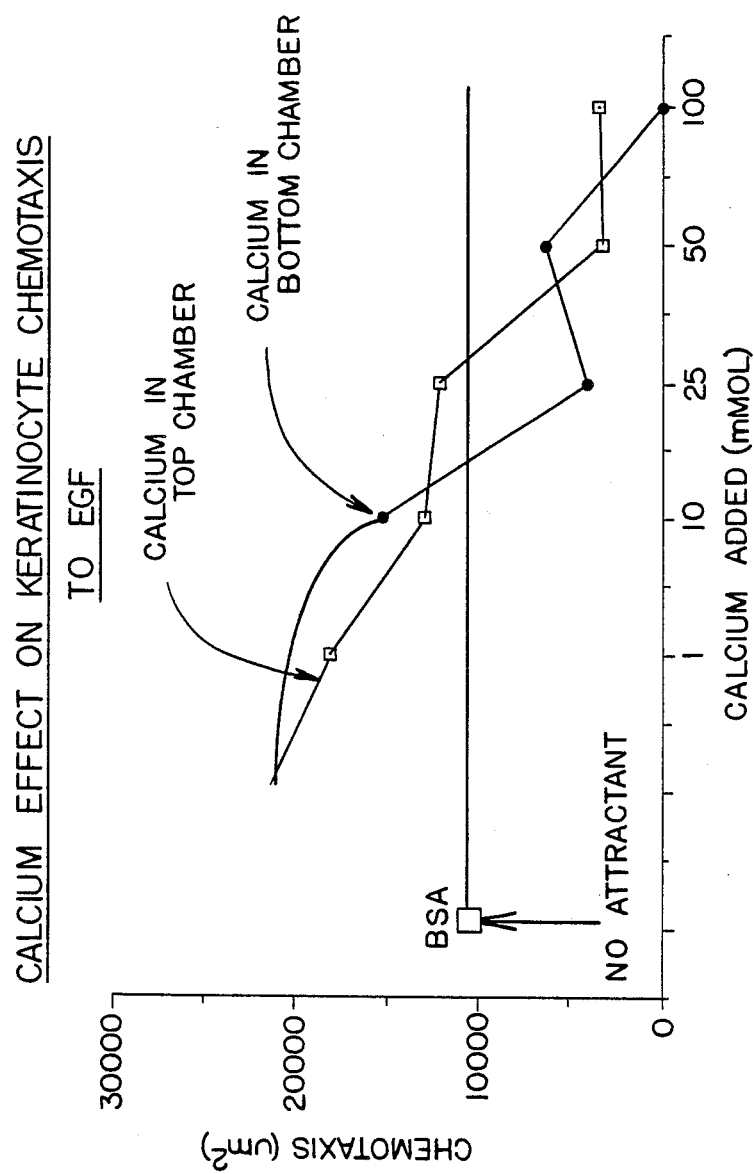
FIG. 6 shows that increasing amounts of calcium ion prevent the keratinocytes from migrating toward attractants. This occurs regardless of the chamber in which the calcium is placed.

As shown in FIG. 6, calcium strongly inhibits the migrating response of cells. These effects were rapid and the cells lost their migratory ability at relatively low levels of calcium. However, as shown in FIG. 5 verapamil, a calcium channel blocker, had no effect on the response of the cells to minoxidil, while a calcium agonist (BAY K8644) did reduce the response of the cells. Therefore, such combinations of drugs may modulate or potentiate the response of the migrating epidermal cells.

Cell adhesion was assayed by adding various amounts of minoxidil to 35 mm tissue culture dishes and 1 ml of serum-free Eagles #2 Medium containing 0.5% BSA. Human keratinocytes were prepared as described above and added to each dish, followed by a two hour incubation at 37° C. in 5% $CO_2$, 95% air. At the end of this period, plates were gently washed three times with PBS to remove unattached cells. Attached cells were trypsinized with 0.025% trypsin, 0.025% EDTA, and electronically counted.

Medical devices can be designed to deliver minoxidil at various concentrations directly to wounds. These might include pastes, gels or emulsions applied directly to the surface of the wound or materials incorporated in a surface covering material or by injection. In general, minoxidil would be supplied in concentrations of 0.01% to 1% in topical application. Methods of preparation and formulations for topical minoxidil are described in U.S. Pat. Nos. 4,139,619 and 4,596,812 herein incorporated by reference. Under other situations, oral administration at levels of 5–100 mg/day could be used alone or in combination with topical treatment.

Minoxidil in the present invention may be used in the form of a liquid, such as eye drops or lotions, or as a salve or gel which may be applied to promote cell migration or attachment, or in any other convenient form. Accordingly, the compound may be contained in any pharmaceutically acceptable carrier which is appropriate for the delivery means intended.

We claim:

1. A method for accelerating the healing of wounds in skin or organs where epidermal cells serve as the source of cells for the coverage of said wounds comprising: treatment of a wound by oral, injection or topical administration with an effective amount of minoxidil whereby the healing process of said wound is accelerated.

2. The method of claim 1 wherein said treatment is a topical composition of minoxidil applied directly to the wound.

3. The method of claim 2 wherein said topical composition comprises from about 0.01% to about 1% minoxidil.

4. The method of claim 1 wherein said treatment is an injection of minoxidil in an effective amount to accelerate the healing of the wound.

5. The method of claim 1 wherein said treatment is an oral administration of minoxidil.

6. The method of claim 5 wherein said oral administration comprises from about 5 to about a 100 mg dose per day of minoxidil.

7. The method of claim 1 wherein said treatment comprises a combination of topical, injection or oral administration of minoxidil.

8. A method for promoting the migration of epithelial cell comprising: treating epithelial cells by oral, injection or topical administration with minoxidil.

9. The method of claim 8 wherein said treatment is a topical composition of minoxidil applied directly to the epithelial cells or the vicinity of the epithelial cells to be effected.

10. The method of claim 9 wherein said topical composition comprises from about 0.01% to about 1% minoxidil.

11. The method of claim 8 wherein said treatment is an injection of minoxidil in an effective amount to promote the migration of the epithelial cells.

12. The method of claim 8 wherein said treatment is an oral administration of minoxidil.

13. The method of claim 12 wherein said oral administration comprises from about 5 to about a 100 mg dose per day of minoxidil.

14. The method of claim 8 wherein said treatment comprises a combination of topical, injection or oral administration of minoxidil.

* * * * *